United States Patent [19]

Stefani et al.

[11] 4,178,298

[45] Dec. 11, 1979

[54] PROCESS FOR PREPARING MALEIC ANHYDRIDE

[75] Inventors: Giancarlo Stefani, Bergamo, Italy; Pietro Fontana, Schaffhausen, Switzerland

[73] Assignee: Lonza, Ltd., Gampel, Switzerland

[21] Appl. No.: 841,533

[22] Filed: Oct. 12, 1977

Related U.S. Application Data

[62] Division of Ser. No. 799,331, May 23, 1977.

[30] Foreign Application Priority Data

May 21, 1976 [CH] Switzerland .................. 6466/76

[51] Int. Cl.$^2$ ............................ C07D 307/60
[52] U.S. Cl. ................. 260/346.75; 252/435; 252/937
[58] Field of Search .................... 260/346.75

[56] References Cited

U.S. PATENT DOCUMENTS

| | | | |
|---|---|---|---|
| 3,156,705 | 11/1964 | Kerr | 260/346.75 |
| 3,156,706 | 11/1964 | Kerr | 260/346.75 |
| 3,156,707 | 11/1964 | Kerr | 260/346.75 |
| 3,238,253 | 3/1966 | Kerr | 260/530 |
| 3,255,211 | 6/1966 | Kerr | 260/346.75 |
| 3,255,212 | 6/1966 | Kerr | 260/346.75 |
| 3,255,213 | 6/1966 | Kerr | 260/346.75 |
| 3,288,721 | 11/1966 | Kerr | 252/435 |
| 3,293,268 | 12/1966 | Bergman et al. | 260/346.75 |
| 3,351,565 | 11/1967 | Kerr | 252/437 |
| 3,352,905 | 11/1967 | Kerr | 260/530 |
| 3,366,648 | 1/1968 | Kerr | 260/346.75 |
| 3,385,796 | 5/1968 | Kerr | 252/437 |
| 3,484,384 | 12/1969 | Kerr | 252/437 |
| 3,888,886 | 6/1975 | Young et al. | 260/346.75 |
| 3,907,833 | 9/1975 | Slinkard et al. | 260/346.75 |
| 3,980,585 | 9/1976 | Kerr et al. | 252/437 |
| 4,049,574 | 9/1977 | Kerr et al. | 252/437 |
| 4,064,070 | 12/1977 | Harrison | 252/435 |
| 4,071,539 | 1/1978 | Kerr et al. | 260/346.75 |
| 4,105,586 | 8/1978 | Kerr | 252/437 |
| 4,123,388 | 10/1978 | Kerr et al. | 252/437 |

FOREIGN PATENT DOCUMENTS

| | | |
|---|---|---|
| 2256909 | 5/1973 | Fed. Rep. of Germany . |
| 2328755 | 1/1974 | Fed. Rep. of Germany . |
| 2353136 | 5/1974 | Fed. Rep. of Germany . |
| 1416099 | 12/1975 | United Kingdom . |

*Primary Examiner*—Alan L. Rotman
*Assistant Examiner*—Bernard Dentz
*Attorney, Agent, or Firm*—Fisher, Christen & Sabol

[57] ABSTRACT

Activated catalyst for oxidation reactions on the basis of mixed oxides of vanadium and phosphorus, characterized in that the vanadium has an average valence of less than +3.9. The activated catalyst is produced using a process wherein a mixed oxide, in which the vanadium has an average valence of +3.9 to more than +4, is activated at temperatures of 300° to 500° C. by passing over it a gaseous hydrocarbon component having 2 to 6 carbon atoms with the exclusion of molecular oxygen. The activated catalyst is used for the production of maleic anhydride from straight-chain $C_4$-hydrocarbons in the gaseous phase.

12 Claims, 1 Drawing Figure

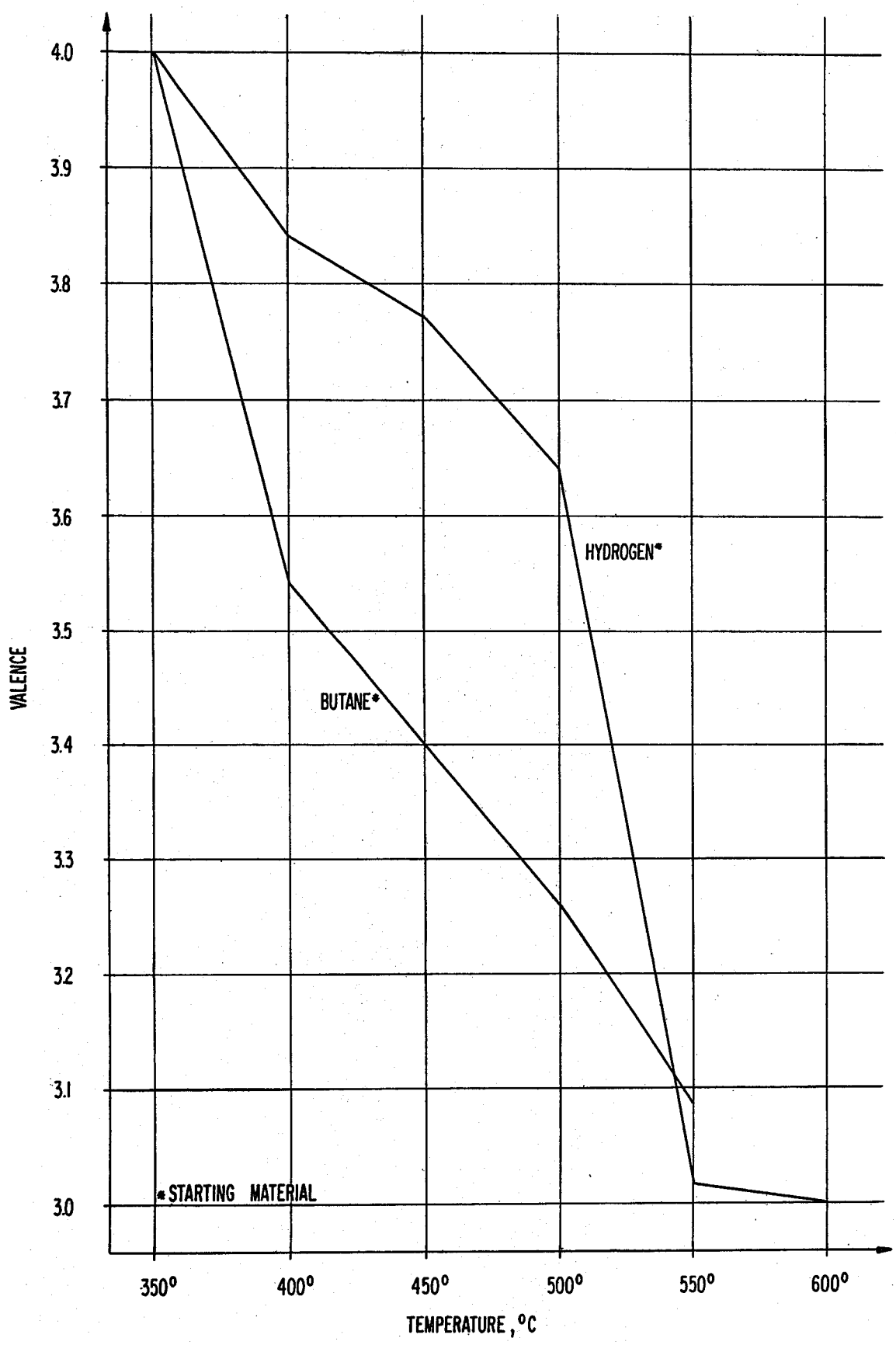

PROCESS FOR PREPARING MALEIC ANHYDRIDE

This is a division of application Ser. No. 799,331, filed May 23, 1977.

BACKGROUND OF THIS INVENTION

1. Field of This Invention

This invention relates to an activated catalyst for oxidation reactions, such catalyst containing a mixed oxide of vanadium and phosphorus, a process for the production of the activated catalyst and a process for using the activated catalyst for producing maleic anhydride from straight-chain C4-hdyrocarbons in the gaseous state.

2. Prior Art

Oxidation catalysts based on mixed oxide of vanadium and phosphorus, which can also contain oxides of other elements, such as, $TiO_2$, are known. See German Patent Nos. 2,256,909 and 2,328,755. Such catalysts are particularly useful for the selective oxidation of butane into maleic anhydride—see U.S. Pat. No. 3,293,268.

According to German Patent No. 2,256,909 the catalyst is brought to an average (median) valence for the vanadium of preferably $+4.1$ to $+4.5$ by a complicated step by step activation in various gases and gas mixtures, for example, with oxygen containing hydrocarbons. The optimal value for the valence of a catalyst, activated in such a manner, lies at $+4.2$. So Table IV of the English Patent No. 1,416,099, which corresponds to German Patent No. 2,256,909, shows that the yields which are achieved with a catalyst, wherein the median valence of the vanadium lies at $+3.9$, drop considerably, and, at a conversion of 39 percent, the yield is only 23 percent by weight.

It is also known that such catalysts quickly become inactive. To achieve reactivation, such catalysts are treated with reduction agents, such as, $H_2$, CO, $CH_4$ and $H_2S$, at a temperature of about 500° C. With such treatment one achieves compensation for the deactivation brought about by over oxidation of the vanadium which reduces the catalyst activity. By means of the reduction treatment, the average valence of the vanadium is adjusted to $+4.2$ to from $+4.6$—see German Patent No. 2,353,136.

Such catalysts, even if they are reactivated, achieve yields of at most about 75 percent by weight in the case of oxidation of butane to maleic anhydride—see German Patent No. 2,353,136.

BROAD DESCRIPTION OF THIS INVENTION

An object of this invention is to provide an activated catalyst for oxidation reactions. Another object of this invention is to provide a process for preparing the activated catalyst. A further object of this invention is to provide a process for using the activated catalyst for producing maleic anhydride from straight-chain C4-hydrocarbons in the gaseous state. Other objects and advantages of this invention are set out herein or are obvious herefrom to one ordinarily skilled in the art.

The objects and advantages of this invention are achieved by the catalyst and processes of this invention.

Higher yields are achieved with catalysts activated in accordance with this invention than with catalysts activated in accordance with the means set out in the above prior art section.

The catalysts activated in accordance with this invention are characterized in that the vanadium has an average valence of less than $+3.9$. Preferably the average (median) valence is between $+3.5$ to $+3.85$.

Preferably the atomic ratio of phosphorus to vanadium is between 1.05 to 1 and 1.10 to 1. Besides phosphorus and vanadium oxides, oxides of other elements, such as Ti, Bi, Cd, Mo, Sb, Zr and Hf can be present in the mixed oxide catalyst.

The activated mixed oxide catalyst of this invention is produced, for example, by combining the individual catalyst components as solutions, for example, hydrochloric acid solutions, by either precipitating them or evaporating them to dryness and calcining and by subjecting the catalyst finally to a heat treatment with a gaseous hydrocarbon having 2 to 6 carbon atoms in the absence of a molecular oxygen.

At the same time the catalyst masses may be used as such or applied to carrier materials. Advantageously, the catalysts are put into effective form, for example, into pressed pellets, tablets and cylinders, and are subsequently subjected to a heat treatment with gaseous hydrocarbons having 2 to 6 carbon atoms. The heat treatment is carried out preferably using gaseous hydrocarbons at a temperature of 300° to 500° C., preferably of 350° to 480° C.

The gaseous hydrocarbons having 2 to 6 carbon atoms preferably are those which are precursors of (i.e., represent a preliminary step of) maleic anhydride. Such gaseous hydrocarbons include butane, butene, butadiene and mixtures thereof. Preferably a mixture of butane and inert gas is used.

The term inert gas, in the sense of this invention, are gases or gaseous mixtures which are free of oxygen (thus not oxidizing) and thus do not enter into any kind of oxidation reaction with the catalyst mass. Such inert gases are, for example, $CO_2$ and preferably $N_2$. It is advantageous to use a mixture of butane with nitrogen, the mixture containing at least 5 percent of butane.

The activated mixed oxide catalyst of this invention can, however, also be produced from already-deactivated catalysts, wherein the vanadium has an average valence of from $+3.9$ to above $+4$, by subjecting it to a heat treatment with butane free of oxygen.

As a result of the heat treatment with butane, according to this invention, a part of the vanadium is converted at a temperature of 300° to 400° C. to vanadium having a valence of $+3$. In the case of the use of the preferred heat treatment of 400° to 450° C., the share of $V_2O_3$, related to the above-mentioned vanadium oxide, already is about 40 to 60 percent.

According to the process of this invention, therefore, the desired activated mixed catalyst can be produced at temperatures which correspond approximately to the temperatures of the oxidation of butane to maleic anhydride. Be it by activation of newly produced mixed oxide or be it by reactivation of catalyst that has already been used, such fact means considerable technical progress in the method of operation since the activation or reactivation can be carried out directly in the oxidation reaction used for the production of maleic anhydride. A once-used catalyst can again be converted into the activated catalyst of this invention (i.e., where the vanadium has an average valence of less than $+3.9$) simply by corresponding changes in the gas supply, i.e., turning off the oxidizing gas and supplying butane/nitrogen.

This is contrary to the state of the prior art (German Patent No. 2,353,136), according to which the reactivation process is based on the use of $H_2$, $CO$, $CH_4$ and $H_2S$ and according to which temperatures of about 500° C. are needed to achieve effective reactivation. Therefore, such reactivation can not be carried out in the reactor in which the oxidation reaction is carried out, in view of the insufficient durability of the construction material. Therefore, the deactivated catalyst must be transferred into a furnace for treatment (reactivation).

The activated catalysts of this invention serve especially well for the oxidative production of maleic anhydride from straight-chain $C_4$-hydrocarbons, such as, butane, butene and butadiene. Preferably n-butane is used.

The reaction temperature is preferably between 350° and 450° C.

In the drawing, the FIGURE is a graph of valence versus temperature.

In the FIGURE, the treatment of a catalyst with n-butane (50 percent in $N_2$) and $H_2$(50 percent in $N_2$) for 24 hours are contrasted. One can see clearly that the same degree of reduction in case of hydrogen occurs only at much higher temperatures. In the case of where an average valence of the vanadium is +3.6 to +3.7, a temperature of 380° to 390° C. will suffice for n-butane, while a temperature of 480° to 510° C. is needed for $H_2$.

DETAILED DESCRIPTION OF THIS INVENTION

As used herein, all parts, weights and percentages are on a weight basis unless otherwise stated herein or otherwise obvious herefrom to one ordinarily skilled in the art.

EXAMPLE 1

1000 gm. of $V_2O_5$ was suspended in 8000 gm of 37 percent HCl. The suspension was heated carefully to 100° C. with stirring, and was then boiled for 2 hours under reflux.

Then 70 gm. of anhydrous oxalic acid, dissolved in 700 ml of water, and finally 1370 gm. of 85 percent $H_3PO_4$ were added slowly. The admixture was concentrated to volume of about 2600 ml. Then 2000 ml water was added to the resultant viscous solution. At the same time, a bright blue crystalline precipitate was obtained which was filtered off and washed with water. The mother liquor was kept for another charge. The atomic ratio P/V in the filtered residue was 1.08 to 1. This solid body (filtrate residue) was dried at 100° C. Natrosol (hydroxy-ethyl-cellulose) in water was used to make the dried filtrate residue into a paste. The paste was shaped into cylinders and heated to 450° C. for 6 hours in the presence of nitrogen for calcination.

A part of the catalyst was activated by a twelve-hour treatment with a butane-nitrogen mixture (50 vol. percent butane) at 400° C. A second part was treated with the same gaseous mixture for 12 hours at 480° C. A third part was treated for 12 hours at 400° C. with hydrogen and nitrogen (50 vol. percent hydrogen). A fourth part was treated with the same hydrogen/nitrogen mixture for 24 hours at 500° C. Finally, a fifth part, after calcination in the presence of nitrogen, was not subjected to any activating treatment.

The medium vanadium-valence was determined for each sample—see the following Table.

EXAMPLE 2

A V-P-O mixed oxide filling was produced as in Example 1, wherein the ratio of P/V also was 1.08 to 1. Again, this mixed oxide was dried at 100° C.

In the further course of the process, an aqueous solution of $TiCl_4$ was prepared and mixed with aqueous ammonia, while stirring, until a pH of 10 was reached. The precipitate obtained thereby was filtered off and washed with water. The resultant filter residue was prepared into a $TiO_2$ paste, which contained about 20 percent of $TiO_2$ and 80 percent of water. 1000 gm of the above-described dried V-P-O complex was mixed with 150 gm of $TiO_2$ paste (corresponding to 30 gm. of $TiO_2$). The admixture was made into a paste using Natrosol (aqueous solution), and the paste was shaped into cylinders. The cylinders were dried in air at 100° C. and subsequently calcined for 6 hours in air at 450° C. Subsequently, the cylinders were activated by passing over them a butane-nitrogen mixture for 15 hours at 450° C. The vanadium was present at an average valence of +3.4.

EXAMPLE 3

A catalyst, prepared as in Example 2, and wherein after deactivation, the average valence of the vanadium had risen to +4, was divided into parts. One part of the catalyst was activated by passing over it a 50:50 mixture of butane and nitrogen for 15 hours at a temperature of 350° C. The other part of the catalyst was activated at 450° C. The vanadium, after such activations had respectively, a valence of +3.9 and 3.4.

EXAMPLES 4 TO 11

The catalysts of Examples 1 to 3 were examined for their behaviour during catalytic oxidation of different $C_4$-hydrocarbons, especially n-butane with air. In the examples, the contact times moreover were varied.

A steel pipe of 25 mm diameter and about 5 m length, which always contained at least 1 kg of catalyst filling, served as the reactor. Salt melts were used as the heat transfer agent. The results are summarized in the following Table. The temperatures stated therein refer to the salt melt and correspond to those temperatures at which the highest yield of maleic anhydride (related to $C_4$-hydrocarbon used) was obtained.

TABLE

| Example No. | Catalyst | Activation | | | | Oxidation | | |
|---|---|---|---|---|---|---|---|---|
| | | Reducing Agent** | Reducing Temperature, °C. | Duration of Reduction, hrs. | Average Valence of the Vanadium | Salt Bath Temp., °C. | Butane Conversion Percent | MA yield referred to butane fed (wt. %) |
| 4 | 1 | Butane | 400° | 12 | 3.5 | 380° | 75 | 82 |
| 5 | 1 | Butane | 480° | 12 | 3.3 | 370° | 76 | 92 |
| 6 | 1 | Hydrogen | 400° | 12 | 3.9 | 395° | 75 | 69 |
| 7 | 1 | Hydrogen | 500° | 12 | 3.7 | 385° | 77 | 74 |
| 8 | 2 | Butane | 450° | 15 | 3.4 | 375° | 75 | 93 |
| 9 | 3 | Butane | 350° | 15 | 3.9 | 390° | 73 | 72 |
| 10 | 3 | Butane | 450° | 15 | 3.4 | 372° | 74 | 91 |

TABLE-continued

| Example No. | Catalyst | Activation | | | | Oxidation | | |
| --- | --- | --- | --- | --- | --- | --- | --- | --- |
| | | Reducing Agent** | Reducing Temperature, °C. | Duration of Reduction, hrs. | Average Valence of the Vanadium | Salt Bath Temp., °C. | Butane Conversion Percent | MA yield referred to butane fed (wt. %) |
| 11* | 1 | | No pre-treatment | | 4.0 | 395° | 77 | 70 |

Notes:
*Comparison example
**Mixture of reducing agent/$N_2$ is 50:50

What is claimed is:

1. Process which comprises converting a straight-chain $C_4$-hydrocarbon in the gaseous phase to maleic anhydride using an activated catalyst, which can be reactivated, for oxidation reactions on the basis of a mixed oxide of vanadium and phosphorus, said vanadium having an average valence of less than +3.9, said catalyst having been activated at a temperature of 300° to 450° C. by passing over the mixed oxide a gaseous hydrocarbon component, which has 2 to 6 carbon atoms, in the absence of molecular oxygen, said catalyst having been calcined before activation, and said catalyst having an atomic ratio of phosphorus to vanadium between 1.05 to 1 and 1.10 to 1.

2. Process as claimed in claim 1 wherein said mixed oxide also contains oxides of elements other than vanadium and phosphorus.

3. Process as claimed in claim 1 wherein said mixed oxide also contains titanium dioxide.

4. Process as claimed in claim 1 wherein said straight-chain $C_4$-hydrocarbon is gaseous n-butane.

5. Process as claimed in claim 1 wherein said vanadium has an average valence between +3.5 and +3.85.

6. Process which comprises converting a straight-chain $C_4$-hydrocarbon in the gaseous phase to maleic anhydride using an activated catalyst, which can be reactivated, for oxidation reactions on the basis of a mixed oxide of vanadium and phosphorus, said vanadium having an average valence of less than +3.9, said catalyst having been activated at a temperature of 300° to 450° C. by passing gaseous butane or a mixture of gaseous butane and a non-oxidizing inert gas over the mixed oxide in the absence of molecular oxygen, said catalyst having been calcined before activation, and said catalyst having an atomic ratio of phosphorus to vanadium between 1.05 to 1 and 1.10 to 1.

7. Process as claimed in claim 6 wherein said mixed oxide also contains oxides of elements other than vanadium and phosphorus.

8. Process as claimed in claim 6 wherein said mixed oxide also contains titanium dioxide.

9. Process as claimed in claim 6 wherein said straight-chain $C_4$-hydrocarbon is gaseous n-butane.

10. Process as claimed in claim 6 wherein said vanadium has an average valence between +3.5 and +3.85.

11. Process as claimed in claim 6 wherein said inert gas is $CO_2$ or $N_2$.

12. Process as claimed in claim 6 wherein said inert gas is $N_2$ and said mixture contains at least 5 percent of butane.

* * * * *